United States Patent [19]

Bohmholdt et al.

[11] Patent Number: 5,360,931
[45] Date of Patent: Nov. 1, 1994

[54] CONTINUOUS MULTI-STAGE PROCESS FOR THE PREPARATION OF (CYCLO) ALIPHATIC DIISOCYANATES

[75] Inventors: Gerd Bohmholdt, Marl; Wilhelm Heitmann, Herne; Peter Kirchner, Bochum; Hans-Werner Michalczak, Herne, all of Germany

[73] Assignee: Huels Aktiengesellschaft, Marl, Germany

[21] Appl. No.: 42,282

[22] Filed: Apr. 2, 1993

[30] Foreign Application Priority Data

May 5, 1992 [DE] Germany .............................. 4214236
Sep. 19, 1992 [DE] Germany .............................. 4231417

[51] Int. Cl.⁵ .......................................... C07C 263/00
[52] U.S. Cl. .................................... 560/344; 560/345
[58] Field of Search ................................ 560/344, 345

[56] References Cited

U.S. PATENT DOCUMENTS

| | | |
|---|---|---|
| 2,677,698 | 5/1954 | Deutschman . |
| 4,287,132 | 9/1981 | Mameniskis et al. ............. 260/453 |
| 4,386,033 | 5/1983 | König et al. ............. 260/453 |
| 4,530,796 | 7/1985 | Mattner et al. ............. 260/453 |
| 4,596,678 | 6/1986 | Merger et al. ............. 560/344 |
| 4,692,550 | 9/1987 | Engbert et al. ............. 560/345 |
| 5,087,739 | 2/1992 | Bohmholdt ............. 560/345 |

FOREIGN PATENT DOCUMENTS

| | | |
|---|---|---|
| 0018586 | 11/1980 | European Pat. Off. . |
| 0054817 | 6/1982 | European Pat. Off. . |
| 0126299 | 11/1984 | European Pat. Off. . |
| 0355443 | 2/1990 | European Pat. Off. . |
| 3314790 | 10/1984 | Germany . |

*Primary Examiner*—José G. Dees
*Assistant Examiner*—Samuel Barts
*Attorney, Agent, or Firm*—Oblon, Spivak, McClelland, Maier & Neustadt

[57] ABSTRACT

A continuous multistage process for the preparation of (cyclo)aliphatic diisocyanates comprising a) condensing urea with a (cyclo)aliphatic diamine in the presence of an alcohol solvent to make a (cyclo)alkylenebisurea in a distillation reactor; b) reacting the crude (cyclo)alkylenebisurea with alcohol in a pressurized distillation reactor to make (cyclo)biscarbamate; c) removing the ammonia formed in the pressurized distillation reactor; d) cleaving the (cyclo)biscarbamate in the presence of a catalyst in a combined cleavage and rectifying column to make crude (cyclo)alkylene diisocyanate; e) reacting a diverted portion of the cleavage products with the alcohol to form a recycling mixture; f) and distilling the crude (cyclo)alkylene diisocyanate formed in step d.

25 Claims, 1 Drawing Sheet

CONTINUOUS MULTI-STAGE PROCESS FOR THE PREPARATION OF (CYCLO) ALIPHATIC DIISOCYANATES

BACKGROUND OF THE INVENTION

1. Field of the Invention

The present invention relates to a multi-stage process for the continuous phosgene-free preparation of (cyclo)aliphatic diisocyanates.

2. Discussion of the Background

Diisocyanates are useful chemical compounds which allow controlled polyaddition, of polymers such as polyurethane and polyureas, which are widely employed industrially in and uses such as foams, elastomers, thermoplastics, fibers, coatings and adhesives. Large industrial scale production of diisocyanates has previously been accomplished by the phosgenation of the diamines, using phosgene. Phosgene is notoriously difficult to manage industrially due to its corrosivity, high toxicity and high chlorine content.

A number of processes for the preparation of (cyclo)aliphatic (in the present invention, the term "(cyclo)aliphatic" corresponds to linear or branched aliphatic or cycloaliphatic) isocyanates which by-pass the use of phosgene are known. In particular these processes first convert the diamines on which the diisocyanates are based, into biscarbamates and subject the diisocyanates to thermal cleavage in a subsequent step. By avoiding the use of phosgene, these processes avoid serious environmental protection problems and an increased expenditure on safety while, at the same time, obtaining chlorine-free isocyanates. These chlorine-free isocyanates are particularly advantageous during later use in production of polyurethanes, since the absence of residual chlorine helps to avoid stress-cracking and other types of corrosion in the reaction vessels used. While these advantages are obtained in the conventional methods, each of the known methods has one or more disadvantage.

EP-PS 18,586, and EP-PS 126,300 each disclose the preparation of (cyclo)aliphatic biscarbamates in a one-pot reaction from urea, diamine and alcohol at temperatures of 160° to 300° C. with simultaneous removal of ammonia.

However, this simultaneous reaction of urea, diamine and alcohol provides poor reaction selectivity. The selectivity of the reaction to produce biscarbonates is reduced by side reactions which proceed unavoidably in the 160°–300° C. temperature range. In addition to the desired biscarbamates, considerable amounts of N-unsubstituted alkyl carbamate and dialkyl carbonate are formed by reaction of urea and alcohol, and polyureas are formed by N,N'-substitution of the urea by the diamine. These by-products must then be removed before thermal cleavage of the biscarbamates, thus requiring an additional step in the process.

EP-PS 27,953 likewise describes a one-stage process for the preparation of carbamates by reaction of urea, primary amines and alcohols, in which the yields are said to be increased by addition of N-unsubstituted carbamates and/or N-mono- or N,N'-disubstituted ureas or polyureas, which are present as intermediate products in this reaction anyway. However, this process does not produce industrially satisfactory yields.

EP-PS 28,331 discloses the preparation of biscarbamates, inter alia, by reaction of linear polyureas with alcohol in the presence of an N-unsubstituted carbamate and/or urea. This is said to prevent the formation of amines which are formed during the reaction of N,N'-disubstituted ureas with alcohol. Once again, however, the yields achieved are not industrially satisfactory.

Additionally, neither EP-PS 27,953 nor EP-PS 28,331 contains examples or indications of the reaction of bisureas with alcohol in the absence of a diamine and/or urea.

The preparation of N-monosubstituted carbamates from trisubstituted ureas and hydroxy compounds is described in DE-PS 2,258,454. U.S. Pat. No. 2,677,698 discloses a two-stage preparation monocarbamates by formation, in the first stage, of N,N'-disubstituted ureas from urea and amine without a solvent, with the carbamates being formed in the second stage upon the addition of monoalcohols.

EP-PS 126,299 discloses a continuous preparation of biscarbamates which uses a three-stage cascade of stirred tanks. The use of a cascade of stirred tanks requires, in each case, a regulated energy supply, a column for removing the ammonia formed during reaction and equipment for maintenance of pressure for each stage, and therefore a high total investment is required.

A semi-continuous preparation of biscarbamates has been described in EP-A 355,443, wherein alternately operated stirred reactors are used and work up (isolation, distillation, etc.) is carried out continuously. The discontinuous charging and emptying required in the use of a series of alternately operated stirred reactions involves undesirable additional operating and apparatus expenditure.

U.S. Pat. Nos. 2,145,242 and 2,445,518 each disclose the preparation of bisureas from urea and diamine in bulk at 130° to 140° C. in 3 to 4 hours with high yields. However, each method suffers from the disadvantage that, under the reaction conditions disclosed, bisureas are obtained as solids, which presents considerable process technology problems for further processing. In order to overcome this problem, it has been proposed to carry out the reaction in the presence of inert diluents or solvents, such as chlorinated benzenes, phenols and cresols (see U.S. Pat. No. 2,145,242 and JP-Sho 38-20-748), or water (see U.S. Pat. No. 2,213,578 and Bachmann et al., J. Am. Chem. Soc. 72 (1950), 3132). However, when these insert solvents or diluents are used, they must then be removed to allow further processing of the bisurea after its formation.

JP-Sho 38-20748 describes the preparation of chain-like condensation resins having urethane bonds and urea bonds. In the disclosed process, diamine and urea are reacted in the presence of diol, at temperatures of 100° to 130° C., in a first reaction stage to give a solid reaction product, which, in addition to minor amounts of the bisurea, contains more highly condensed products of the linear polyurea type. These highly condensed products of the linear urea type have internal urea groupings —NH—CO—N—, which remain stable during condensation to the polyurea-polyurethane at 230° C. in the presence of the diol.

It is also known from EP-PS 18,586 that the reaction of urea with hexamethylenediamine in the presence of butanol at 120° to 150° C. gives polyhexamethyleneurea, which is then insoluble in butanol at a temperature of 190° C. and cannot be converted into the biscarbamate.

Thermal cleavage of (cyclo)aliphatic biscarbamates can be carried out in the gas phase or in the liquid phase, with or without solvents and with or without catalysts. EP-PS 126,299 and 126,300 describe processes for the preparation of hexamethylenediisocyanate and isophorone diisocyanate, respectively, by cleavage of the corresponding biscarbamates in the gas phase in a tubular reactor in the presence of metallic packing at 410° C. In addition to the fact that such high temperatures can be established only with expensive technology, the disclosed processes have the disadvantage that partial cracking of the reaction products takes place at this high temperature, causing deposits on the packing and blocking of the tubular reactor. Because of this partial cracking, the process and apparatus have a short service life, making the process unsuitable for industrial production.

A continuous process for the cleavage of (cyclo)aliphatic biscarbamates in the liquid phase in the presence of catalysts without solvents is described in EP-A 355,443. In this process, 1,5-diisocyanato-2-methylpentane and other (cyclo)aliphatic diisocyanates are prepared in high yield in a stirred reactor having a capacity of 200 g, with intensive boiling of the reaction mixture at 233° C. under 27 mbar. A major disadvantage to this process occurs during scale-up, in that the enlargement of the cleavage reactor, necessary to increase the capacity, leads to a reduction in the ratio of heat transfer surface of the reactor to the volume of reactor contents. If the specific heating capacity of the reactor remains unchanged, the wall temperature must be increased, leading to decomposition and caking and to deterioration of the heat transfer capability. This process is therefore also unsuitable for industrial production.

Another continuous process for the cleavage of (cyclo)aliphatic biscarbamates is disclosed in EP-A 323,514, where isophorone diisocyanate is prepared in good yield from the corresponding biscarbamate in a 300 ml flask, surmounted by a column, in the presence of 100 g of partly hydrogenated terphenyl and manganese acetate as catalyst. Once again, an attempt to scale up this process causes the yield to deteriorate considerably when the capacity is increased, because of the less favorable ratio of heat transfer surface to contents, making this process also unsuitable for industrial use.

EP-PS 54,817 discloses the continuous cleavage of monocarbamates in the liquid phase without a solvent, removal of unreacted monocarbamate and isolation of the monoisocyanate cleavage products from the alcohol used in the cleavage. However, this process leads to good results only if dephlegmators are used. If a distillation column with removal of a side stream is employed, the cleavage products cannot be isolated at all or can be isolated in only a very poor yield. Because of the low separation efficiency of dephlegmators, the condensates contain the desired components of isocyanate and alcohol in only moderate purity. During further processing of the condensates, the isocyanate thus recombines with the alcohol to give the carbamate, which must be recycled again into the cleavage reaction, causing an inherent inefficiency in the process. The profitability of the process suffers as a result.

In EP-PS 61,013, the cleavage of bis- and polycarbamates in the presence of solvents and auxiliaries, such as hydrogen chloride or organic acid chlorides, is disclosed with the cleavage products being partly condensed using dephlegmators as in EP-PS 54,1317. Because of the use of solvents and auxiliaries, which are volatile under the reaction conditions and lead to contamination of the cleavage products, the profitability of the process deteriorates still further beyond that caused by the use of dephlegmators.

In EP-PS 92,738, carbamate cleavage is carried out in a thin film in a tubular reactor or thin film evaporator, in which secondary reactions are said to be suppressed by a single pass and a short residence time. Since these secondary reactions cannot be completely avoided, in spite of the presence of a catalyst and/or stabilizer, solvents are employed to prevent caking in the tubular reactor. The gaseous cleavage products are partly condensed using dephlegmators connected in series. Cleavage to give isophorone diisocyanate, as described in EP-PS 92,738, shows the disadvantages of the process. The crude isophorone diisocyanate removed from the second dephlegmator contained only 55.5% of isophorone diisocyanate. Additionally, 43.2% of monoisocyanato-monocarbamate, and 22.6% of biscarbamate were identified in the subsequently condensed crude butanol. The yield of isophorone diisocyanate was only 51.8% of the theoretical yield.

In EP-A 396,977, as in the above-mentioned EP-PS 92,738, carbamate cleavage is performed in a tubular reactor in the presence of a solvent and catalyst. The gaseous cleavage products are likewise removed by partial condensation in dephlegmators connected in series. The diisocyanate fraction—after further dilution with the solvent employed for the cleavage—is then extracted with hydrocarbons. Because the partition coefficients of isophorone diisocyanate (IPDI) and monoisocyanato-monocarbamate (IPIU) differ only slightly, however, only incomplete separation of these compounds is possible, in spite of multi-stage extraction. The process thus becomes even more uneconomical, since an additional substance is moreover introduced into the process with the extraction agent and must be recovered in a subsequent separating operation, requiring an additional investment.

EP-A 396,976 differs from EP-A 396,977 in that the cleavage is carried out either in a tubular reactor or discontinuously in a stirred reactor, the temperature and pressure being chosen such that only the alcohol is distilled off. The bottom product from the tubular reactor or the product from the stirred reactor is then worked up by extraction and distillation, so that this process is also similarly uneconomical.

Summarizing, it can be said that the cleavage of carbamates in the gas phase has a fundamental disadvantage of exposure of the reaction products to high temperatures, while cleavage in the liquid phase in the presence of solvents requires a higher energy consumption and, because of the lower space/time yield, correspondingly higher investment compared with cleavage in the liquid phase without a solvent. The dephlegmators employed for partial condensation do not operate effectively with regard to satisfactory separation of isocyanate and alcohol.

A process is needed which provides for the preparation of (cyclo)aliphatic diisocyanates which does not have the above-mentioned disadvantages.

SUMMARY OF THE INVENTION

One object of the present invention is to provide an improved process for the preparation of (cyclo)aliphatic diisocyanates which avoids the use of high temperatures and maintains high space/time yields.

A further object of the present invention is to provide a multistep continuous process for the production of (cyclo)aliphatic diisocyanates which avoids the production of unwanted by-products.

These and other objects have been satisfied by the discovery of a continuous process for production of (cyclo)aliphatic diisocyanates in which the formation of bisureas under specific conditions is carried out in the first step, the formation of biscarbamates is carried out in the second step and the cleavage of the biscarbamates in the liquid phase to give the diisocyanates is carried out in the third step.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawing, wherein.

DETAILED DESCRIPTION OF THE PREFERRED EMBODIMENTS

Figure 1:
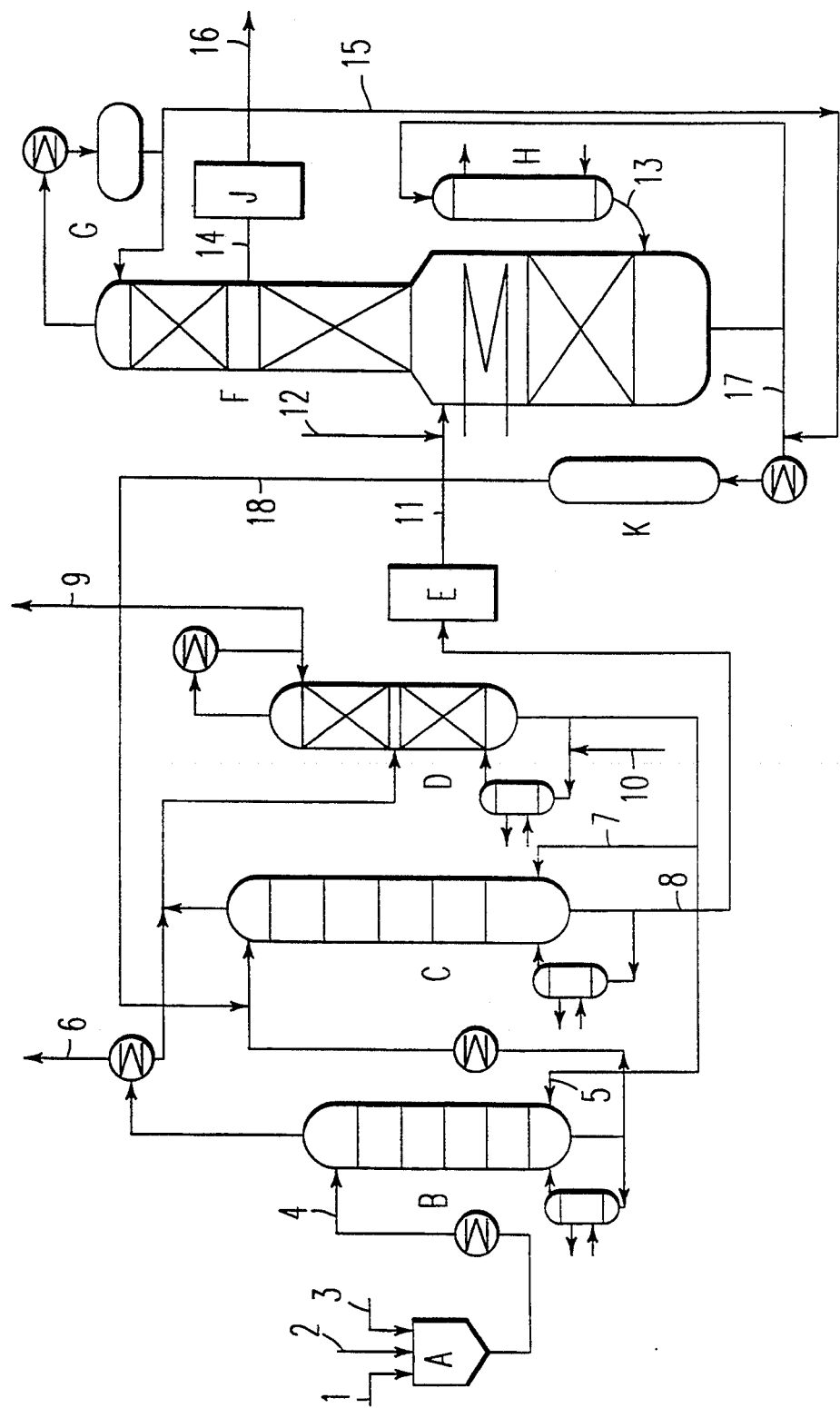
FIG. 1 shows a simplified flow diagram for the process of the present invention.

The present invention relates to a continuous multistage process for the preparation of (cyclo)aliphatic diisocyanates of the formula $$OCN-R^1-NCO$$

wherein $R^1$ represents a linear or branched aliphatic hydrocarbon radical having a total of 6 to 12 carbon atoms preferably 6–10 carbon atoms, or a cycloaliphatic hydrocarbon radical having a total of 6 to 13 carbon atoms—preferably 6–10 carbon atoms which may contain a substituent, wherein the process comprises the steps of:

(a) condensing urea with a (cyclo)aliphatic diamine of the formula $$H_2N-R^1-NH_2$$

in the presence of an alcohol of the formula $$R^2-OH$$

as solvent, to give a (cyclo)alkylenebisurea of the formula $$H_2N-CO-NH-R^1-NH-CO-NH_2$$

wherein, $R^1$ is as described above and $R^2$ represents a primary aliphatic hydrocarbon radical having 3 to 5 carbon atoms preferably 3 to 4 carbon atoms, where the condensation is performed in a distillation reactor at 100° to 130° C. under a pressure of 0.7 to 1.5 bar (absolute), wherein the reagents are introduced continuously onto the top tray of the distillation reactor, and the ammonia formed being driven off by codistillation with the alcohol vapors added to the bottom of the column, (b) reacting the crude (cyclo)alkylenebisurea obtained with the alcohol employed as solvent in (a) to give a (cyclo) alkylene biscarbamate of the formula $$R^2-O-CO-NH-R^1-NH-CO-O-R^2$$

wherein $R^1$ and $R^2$ are as described above, and wherein the reaction is performed in a pressurized distillation reactor which is operated at temperatures of 160° to 210° C. at the top and at 180° to 250° C. at the bottom, under a pressure of 7 to 13 bar, wherein the reaction mixture from step (a) is introduced onto the top tray of the column together with the reaction mixture from process stage (e) below, and the ammonia formed being driven off by codistillation with the alcohol vapors added to the bottom of the column, and the crude (cyclo)alkylene biscarbamate is purified by conventional distillation, (c) removing ammonia from the vapors obtained at the top of the pressurized distillation reactor of step (b), and from the alcohol obtained by partial condensation of the vapors from step (a), in an alcohol recovery column, which is under the same pressure as the pressurized distillation reactor of step (b), with the ammonia-free alcohol obtained at the bottom of the column being recycled to the bottom of the distillation reactor of step (a) and to the bottom of the pressurized distillation reactor of step (b), (d) cleaving the purified (cyclo)alkylene biscarbamate, in the presence of a catalyst, without using solvents, in a combined cleavage and rectifying column, wherein the cleavage is carried out in the lower part of the column to provide a mixture of cleavage products, with a portion of the cleavage products stream being diverted, and wherein rectification of the cleavage products is carried out in the upper part of the column, so that pure alcohol is obtained at the top and crude (cyclo)alkylene diisocyanate is obtained in a lateral take-off from the cleavage and rectifying column, (e) reacting the diverted portion of the cleavage products stream from step (d) with the pure alcohol from step (d) and recycling the resultant reaction mixture into the pressurized distillation reactor of step (b), and (f) distilling the crude (cyclo)alkylene diisocyanate to provide the pure (cyclo)alkylene diisocyanate.

Surprisingly, it has been found that urea can be reacted with a diamine, in the presence of an alcohol as solvent, to give a bisurea if the reaction is carried out at temperatures below the decomposition point of urea, preferably from 100° to 130° C., for a period of 4 to 10 hours, preferably 6 to 8 hours. The ammonia formed during reaction is removed concurrently with its formation. The bisurea formed can then be converted essentially quantitatively into the biscarbamate at higher temperatures of 160° to 250° C., preferably 180° to 230° C., using the alcohol employed in the first reaction.

By preparing the biscarbamate in two separate stages at different temperature and pressure ranges, it is possible to react urea selectively with the diamine at relatively low temperatures and to suppress the formation of by-products, thus overcoming the disadvantages of EP-PS 18,586, EP 126,299 and 126,300 and EP-A 355,443 as discussed above.

Surprisingly, the reaction of diamines with urea takes place selectively in the presence of an alcohol at temperatures below 130° C. to give the bisurea, contrary to the disclosures in EP-PS 18,586 and JP-Sho 38-20748.

By using a distillation column and a pressurized distillation reactor, the method of the present invention permits continuous preparation of the biscarbamate while avoiding the disadvantages of a cascade or alternating procedure.

The cleavage of (cyclo) aliphatic biscarbamates in accordance with step (d) of the present invention can be carried out on an industrial scale in a high yield and high purity in the liquid phase. The method is performed in a combined cleavage and rectifying column in the absence of solvents. It is preferred that the combined cleavage and rectifying column be provided with higher activity, preferably structured, packing and with a falling film evaporator at the bottom of the column, from which not more than 20% by weight of the feed evaporates. During operation the liquid and vapors are passed through the column in counter-current fashion. The column is provided with a device for removal of crude diisocyanate from the upper third of the column and with a condenser, condensate collection vessel and reflux pump for the removal of pure alcohol at the top. The cleavage reaction can thus be performed without deposits in the cleavage zone to provide a relatively pure crude diisocyanate and pure alcohol.

(Cyclo)aliphatic diamines, urea and primary aliphatic alcohols are used for carrying out one embodiment of the present invention for continuous preparation of (cyclo)aliphatic diisocyanates.

The (cyclo)aliphatic diamines are organic diamines having aliphatically and/or cycloaliphatically bonded amino groups. Typical examples are branched or linear $C_4$–$C_{20}$ aliphatic diamines such as hexamethylenediamine, 2-methylpentamethylenediamine, octamethylenediamine, 2,2,4- and 2,4,4-trimethylhexamethylenediamine or mixtures thereof, decamethylenediamine, 2-methylnonamethylenediamine and dodecamethylenediamine, and $C_5$–$C_{20}$-cycloaliphatic diamines, such as, for example, 1,4-cyclohexanediamine, 1,3- or 1,4-cyclohexanedimethanamine, 5-amino-1,3,3-trimethylcyclohexanemethanamine (isophoronediamine), 2(4)-methyl-1,3-cyclohexanediamine or 4,4'-methylenebis(cyclohexanamine).

Suitable alcohols include primary aliphatic alcohols which have a sufficiently different boiling point from the particular diisocyanate ($bp_{diisocyanate} \geq bp_{alcohol} + 20°$ C.), and which allow evaporation of the biscarbamate and condensation of the cleavage products under operating pressures which are favorable in terms of process technology. Examples of suitable alcohols include propanol, butanol, isobutanol and pentanol.

The reaction of a diamine with urea, in the presence of an alcohol as solvent, to give the bisurea is carried out in a distillation reactor, with the reactants being introduced continuously onto the top tray of the column. Additional alcohol vapors are added to the bottom of the column to assist in the removal of the ammonia liberated during the reaction. The ammonia/alcohol mixture is partly condensed in a condenser, preferably at temperatures of 30° to 50° C., in order to avoid the precipitation of ammonium carbamate. Ammonia-free alcohol is recovered from the condensate by distillation in a column downstream of the pressurized distillation reactor.

The molar ratio of the starting materials in step (a)—(cyclo)aliphatic diamine: urea: alcohol—is from 1:2.0– 2.4:3–10. The distillation reactor of step (a) has at least 4 trays, preferably at least 8 trays, most preferably at least 10 trays. The reaction is carried out at temperatures of 100° to 130° C. under pressures of 0.7 to 1.5 bar (absolute). The residence time in the distillation reactor is from 4 to 10 hours, preferably 6 to 8 hours. The amount of alcohol introduced into the bottom of the column for driving off the ammonia is from 0.05 to 3 kg/kg of bisurea formed, preferably 0.1 to 1 kg/kg of bisurea formed. The alcohol introduced in this way is removed at the top, together with the ammonia formed during the reaction, partially condensed, freed from residual ammonia in an alcohol recovery column, and recycled to the bottom of the distillation reactor of step (a).

The reaction temperature is limited to not more than 130° C. in order to achieve as complete a reaction of the urea as possible. This allows the production of the bisurea without the formation of (N-unsubstituted) O-alkyl carbamate. The rate of reaction is dependent upon the reaction temperature and the nature and ratio of the starting materials. The reaction rate determines the residence time required to obtain a complete reaction, and therefore the dimensions of the distillation Nectar. As the reaction rate increases, the residence time needed decreases and thus the size of the distillation reactor should be smaller. As the reaction rate decreases the residence time and required reactor size necessarily increase.

The advantage of using a distillation reactor over a cascade of stirred tanks is that the reaction mixture is passed into the top of the distillation reactor in a counter-current fashion relative to the alcohol vapors introduced into the bottom of the column, with each tray in practice corresponding to a cascade stage. The introduction of alcohol vapors causes intensive mixing of the liquid at each individual tray so that stirring devices are no longer necessary. Thus, a reactor is provided which is favorable in terms of energy, operation and investment results. The energy consumption is considerably lower than that of a cascade of stirred tanks, since the alcohol vapors have to be generated and condensed only once. The expenditure on apparatus and on measurement and control is correspondingly low since only one vessel (column) is needed in the case of the distillation reactor while a cascade system required multiple tanks with individual stirring and heating systems.

The crude bisurea dissolved in alcohol and obtained at the bottom of the distillation reactor of step (a) is passed continuously into the top tray of the pressurized distillation reactor of step (b). The feed is brought to the required reaction temperature by a heating means which may be either external or internal to the pressurized reefs. Suitable heating means include an external heat exchanger and an internal immersion heater.

The reaction of the bisurea with the alcohol to give a biscarbamate is carried out under elevated temperature and increased pressure, with the ammonia formed during the reaction being removed in order to drive the reaction equilibrium towards the production of biscarbamate. This is effected by the introduction of alcohol vapors into the bottom of the pressurized distillation reactor. The alcohol vapors are preferably produced in an evaporator located at the bottom of the column.

The advantages of the pressurized distillation reactor over a cascade of stirred tanks are the same as those for the distillation reactor. If a cascade of stirred tanks is used, incomplete conversion and a corresponding loss in yield results unless a large number of stirred tanks is used. This would be highly cost prohibitive compared to the pressurized reactor of the present invention (see also Ullmanns Encyklopadie der technischen Chemie (Ullmann's Encyclopaedia of Industrial Chemistry), 4th edition 1973, volume 3, pages 342–349) .

The rate of reaction of biscarbamate formation is affected by the parameters of temperature, pressure, ratio of bisurea to alcohol, alcohol vapors introduced into the bottom of the pressurized distillation reactor and number of stages of the pressurized distillation rescuer. Pressures of 7 to 13 bar, preferably 10 to 12 bar; temperatures of 180° to 250° C., preferably 200° to 230° C., in the bottom of the pressurized distillation reactor and of 160° to 210° C., preferably 180° to 200° C., at the top of the pressurized distillation reactor; a molar ratio of bisurea to alcohol of from 1:5 to 1:12, preferably 1:7 to 1:10 and alcohol vapors introduced into the bottom of the pressurized distillation reactor in an amount of from 0.5 to 8 kg/kg of biscarbamate formed, preferably 1 to 4 kg/kg of biscarbamate formed, have proven advantageous for the process according to the invention. The average residence time in the pressurized distillation reactor required for complete conversion is 5 to 20 hours, preferably 9 to 14 hours.

Because of the low rate of reaction of the bisurea with the alcohol, a high temperature is desirable. However, the temperature should be limited to not more than 250° C., in order to avoid the formation of by-products. Since the column pressure is stabilized accordingly, the rate of reaction then depends on the alcohol used and the weight ratio between the biscarbamate and alcohol in the bottom of the column. This ratio is preferably 0.5 to 1.7, most preferably 0.8 to 1.2. For example, if butanol is used, and the ratio of biscarbamate to butanol in the bottom of the pressurized distillation reactor is 1:1, with a bottom temperature of 230° C., the bottom pressure is about 11 bar. A temperature of about 200° C. is then established at the top of the column.

The vaporous mixture of alcohol and ammonia removed at the top is passed, without being condensed and preferably under the pressure of the pressurized distillation reactor, into the central region of an alcohol recovery column, in which ammonia-free alcohol is obtained at the bottom of the column by rectification at not less than 170° C., depending on the alcohol chosen and the operating pressure. The ammonia-free alcohol obtained is then recycled into the bottom of the distillation reactor of step (a) and the pressurized distillation reactor of step (b). The ammonia is removed at the top of the rectifying column. To prevent any ammonium carbamate present from being deposited on the reflux condenser of the column, a corresponding amount of alcohol is allowed to exit the top of the column with the ammonia in an amount sufficient to increase the temperature at the top to at least 60° C. The amount of alcohol lost from the column in this way is concurrently replaced by the addition of fresh alcohol to the system.

The biscarbamate/alcohol mixture obtained in the bottom of the pressurized distillation reactor is purified by distillation in a conventional manner. The residual alcohol which is removed during distillation can then be recycled onto the top tray of the distillation reactor of step (a).

Prior to cleavage of the purified biscarbamate, a catalyst is added in an amount of from 5 to 400 ppm, preferably 20 to 100 ppm. Suitable catalysts are halides or oxides of metals of groups IB, IIB, IIIB, IVB, VB, VIB, VIIB and VIIIB of the periodic table, with chlorides of zinc or tin and oxides of zinc, manganese, iron or cobalt being preferred. The catalyst may be added in any form suitable for addition to the reaction medium, with a solution or suspension of the catalyst in the same alcohol used in preparing the biscarbamate being preferred. The solution or suspension may be at any catalyst concentration, with catalyst concentrations of from 0.01 to 10% by weight preferred and concentrations of from 3 to 7% by weight more preferred. Most preferred for ease of handling is a catalyst concentration of about 5% by weight.

The cleavage of the biscarbamate is carried out in a combined cleavage and rectifying column. The cleavage is carried out in the lower part of the column and the cleavage products are rectified in the upper part. The diisocyanate formed is obtained as crude diisocyanate from a means for removing the crude diisocyanate which is located in the upper third of the column, preferably a lateral take-off, while pure alcohol is removed at the top of the column. In order to remove by-products formed during the cleavage, a portion of the reaction mixture is continuously diverted from the bottom of the column in an amount of from 5 to 50% by weight, preferably 15 to 25% by weight, based on the amount of purified biscarbamate as feed. The cleavage is performed under a bottom pressure of 5 to 50 mbar, preferably 20 to 30 mbar, at a bottom temperature of 200° to 260° C., preferably 230° to 240° C. The biscarbamate to be cleaved can be fed either into the circulation to the falling film evaporator of the column or into the lower third of the column, preferably above the energy recovery device of the column.

The combined cleavage and rectifying column is equipped with a falling film evaporator for supplying energy at the bottom, with an energy recovery device in the lower third of the column. The column is also equipped with a means for removing crude diisocyanate in the upper third of the column and with a condenser, condensate collection vessel and pump for the reflux and removal of pure alcohol at the top.

In order to avoid exposure of the biscarbamate to too high a temperature, the falling film evaporator is operated such that, in a single pass, not more than 20% by weight, preferably less than 10% by weight, of the feed evaporates with the liquid and vapors being passed in countercurrent fashion.

Because of the reactivity of the isocyanate groups, their average residence time in the cleavage zone should be made as short as possible. This is achieved by minimizing the volume of liquid in the column by appropriate structural measures and by using structured packing with a low 'hold-up', as well as by distillation of the diisocyanate formed out of the cleavage zone as soon as possible after formation. The distillation of the product diisocyanate is performed by appropriate introduction of energy to the bottom of the combined cleavage and rectifying column. A concentration profile is thereby established in the column, with essentially biscarbamate and less than 3% by weight of diisocyanate being present at the bottom of the column, while the liquid in the lower half of the column comprises only small amounts of biscarbamate, and essentially monoisocyanato-monocarbamate. The necessary reflux to provide such a concentration gradient is generated by a condensation stage which is located above the cleavage zone and below the diisocyanate lateral take-off. This mode of operation is particularly economical, since the energy to be removed here occurs at a relatively high temperature and can then be used again, for example, for heating up the feed products passed into the distillation reactor for the bisurea preparation of step (a). The condensation stage reduces the amount of vapors presented at the top of the column so that the diameter of the column above this partial condenser can be reduced correspondingly.

Despite the prompt distillation of the diisocyanate from the cleavage zone, the formation of higher molecular weight compounds still occurs in trace amounts, so that a corresponding amount of the reaction mixture must be continuously diverted from the bottom of the combined cleavage and rectifying column. These products are passed to a downstream reactor for reaction with the alcohol obtained from the top of the combined cleavage and rectifying column.

The crude diisocyanate removed from the combined cleavage and rectifying column is purified by vacuum distillation in a conventional manner. The first runnings and distillation residue are preferably recycled into the combined cleavage and rectifying column. The stream diverted from the bottom of the combined cleavage and rectifying column and the alcohol removed at the top of this column are mixed continuously and, after heating to 100° to 140° C., reacted in a tubular reactor under a pressure of 1.7–2.3 bar, preferably around 2 bar, over a residence time of 1 to 4 hours, preferably 2 hours, in order to convert the isocyanate groups into carbamate groups. The resulting product is recycled continuously onto the top tray of the pressurized distillation reactor of step (b).

Description of the Plant

The device in which the process according to the present invention was performed according to Examples 1 to 4 is described below with the aid of FIG. 1. The appropriate material streams are given in parentheses.

A mixture (4) of diamine (1), urea (2) and alcohol (3) was passed continuously, preferably using a pump, from the mixing vessel A through a steam-heated preheater onto the top tray of the distillation reactor B under ambient pressure. The average residence time in distillation reactor B was 7 hours. Alcohol (5) was introduced from the bottom of alcohol recovery column D into the bottom of distillation reactor B. The amount of energy supplied to the reboiler of distillation reactor B was regulated such that the amount of alcohol obtained at the top, together with the ammonia (6) formed and condensed in the dephlegmator with hot water at 40° C., corresponded to the amount of alcohol (5) introduced in the bottom. The condensed alcohol was passed continuously into alcohol recovery column D.

The solution of bisurea in alcohol obtained at the bottom of distillation reactor B was fed, under level control, through a preheater, where it was heated up to 190° to 200° C., onto the top tray of pressurized distillation reactor together with the reaction product (18) from reactor K. The average residence time in pressurized distillation reactor C was 10.5 hours. Column C was heated to establish a temperature profile of 229° C. at the bottom and 200° C. at the top. Alcohol (7) was introduced into the bottom of pressurized distillation reactoer C, and the amount of heat transfer oil for the reboiler was regulated such that the amount of alcohol removed at the top, together with the ammonia formed, corresponded to the alcohol (7) introduced in the bottom.

The resulting alcohol/ammonia mixture, from the top of both the distillation reactor B and the pressurized distillation reactor C, was then passed to alcohol recovery column D. The temperature at the top of column D was 85° C. The alcohol losses, which arise by diversion of the ammonia (6 and 9), were replaced by supplying fresh alcohol (10), in a level-controlled manner, to the bottom of column D.

The mixture (8) obtained in the bottom of pressurized distillation reactor C was purified by distillation (E) in a conventional manner.

The combined cleavage and rectifying column F used for cleavage of the biscarbamate was structured as follows: The lower part of the column contained structured packing, with a tubular bundle heat exchanger above the packing. Above the tubular bundle heat exchanger, the column section was constricted to 50% of the lower cross-section and equipped with structured packing, with distribution of liquid in between, and finally with a vapor tube to the top condenser and condensate collection vessel G.

After addition of catalyst (12), the biscarbamate to be cleaved (11) was fed onto the upper tray of the tubular bundle heat exchanger, the pipes of which projected 10 mm above the tube sheet in order to achieve uniform distribution over the entire cross-section. The energy required for the cleavage and rectification was transferred with heat transfer oil in the falling film evaporator H. The vapor/liquid mixture (13) leaving the falling film evaporator separated in the bottom of the combined cleavage and rectifying column F.

The pure alcohol formed during the cleavage and obtained at the top rectification tray was removed, after condensation, from the condensate collection vessel G (15) and passed to reactor K along with the stream (17) diverted from the bottom of the cleavage and rectification column F.

The purified diisocyanate (16) was obtained by conventional vacuum distillation of the crude diisocyanate (14) removed from column F in the lateral take-off.

The product mixture (18) obtained after reaction of isocyanate groups with alcohol at 120° C. over a residence time of about 2 hours in tubular reactor K was then recycled onto the top tray of pressurized distillation reactor C.

EXAMPLES 1 to 4

TABLE 1

| Material stream | | | Example | | | |
|---|---|---|---|---|---|---|
| No. | Designation | Dimensions | 1 | 2 | 3 | 4 |
| 1 | Diamine | | IPD | TMD | MPD | IPD |
| | | kg/h | 23.8 | 20.5 | 14.3 | 18.4 |
| 2 | Urea | kg/h | 17.3 | 16.0 | 15.2 | 13.4 |
| 3 | Butanol | kg/h | 62.2 | 57.6 | 54.7 | 48.1 |
| 4 | Starting materials | °C. | 119 | 119 | 118 | 119 |
| 5 | Butanol | kg/h | 6.9 | 6.4 | 6.1 | 6.2 |
| 6 | Butanol | vol. % | 2.5 | 2.5 | 2.5 | 2.5 |
| 7 | Butanol | kg/h | 56.7 | 52.9 | 51.0 | 51.8 |
| 8 | Biscarbamate:butanol | kg/kg | 1.16 | 1.22 | 1.12 | 1.30 |
| 9 | Butanol | wt. % | 11.1 | 11.1 | 10.0 | 11.0 |
| 10 | Butanol | kg/h | 2.7 | 2.7 | 2.8 | 2.6 |
| 11 | Biscarbamate | kg/h | 65.6 | 63.0 | 54.6 | 55.1 |

TABLE 1-continued

| No. | Material stream Designation | Dimensions | Example 1 | Example 2 | Example 3 | Example 4 |
|---|---|---|---|---|---|---|
| | $n_D^{25}$ | — | 1.4778 | 1.4654 | — | 1.4778 |
| | Melting point | °C. | — | — | 48 | — |
| 12 | 5% of ZnCl$_2$ in butanol | kg/h | 0.13 | 0.12 | 0.11 | — |
| | 5% of ZnO in butanol | kg/h | — | — | — | 0.11 |
| 13 | Evaporation | wt. % | 9.0 | 8.5 | 8.0 | 9.0 |
| | Pressure | mbar | 27 | 27 | 27 | 27 |
| 14 | Crude diisocyanate | kg/h | 32.0 | 28.0 | 21.8 | 24.7 |
| | Butanol | wt. % | 0.53 | 0.62 | 0.95 | 0.85 |
| 15 | Butanol | kg/h | 23.1 | 22.1 | 21.3 | 18.4 |
| 16 | Pure diisocyanate | kg/h | 30.0 | 26.0 | 19.6 | 22.5 |
| | Yield | % | 96.5 | 95.4 | 94.6 | 93.6 |
| | $n_D^{25}$ | — | 1.4832 | 1.4614 | 1.4537 | 1.4832 |
| 17 | Diverted stream | kg/h | 12.5 | 14.8 | 13.6 | 14.1 |
| 18 | Recycled stream | kg/h | 35.8 | 37.1 | 35.1 | 32.7 |
| | NCO content | wt. % | <0.1 | <0.1 | <0.1 | <0.1 |

IPD = 5-amino-1,3,3-trimethylcyclohexanemethanamine
TMD = 2,2,4(2,4,4)-trimethylhexamethylenediamine (mixture)
MPD = 2-methylpentamethylenediamine Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A continuous multi-stage process for the preparation of (cyclo)aliphatic diisocyanates of the formula $$OCN-R^1-NCO$$

wherein R$^1$ represents a substituted or unsubstituted linear or branched aliphatic hydrocarbon radical having a total of 6 to 12 carbon atoms or a cycloaliphatic hydrocarbon radical having a total of 6 to 13 carbon atoms, which may have a substituent, comprising the steps of:

(a) condensing urea with a (cyclo)aliphatic diamine of the formula $$H_2N-R^1-NH_2$$

in the presence of an alcohol solvent of the formula $$R^2-OH$$

to give a (cyclo)alkylenebisurea of the formula $$H_2N-CO-NH-R^1-NH-CO-NH_2$$

wherein R$^1$ is as described above and R$^2$ represents a primary aliphatic hydrocarbon radical having 3 to 5 carbon atoms, wherein said condensing step is performed at 100° to 130° C. under a pressure of 0.7 to 1.5 bar (absolute) in a distillation reactor having at least 4 trays, with said urea, said alcohol and said (cyclo)aliphatic diamine being introduced continuously onto the top tray of said distillation reactor, and wherein an additional amount of said alcohol is introduced to the bottom of said distillation re,crop, with removal of ammonia formed during said condensing step, to form a reaction mixture containing a crude (cyclo)alkylenebisurea, (b) reacting said crude (cyclo)alkylenebisurea with said alcohol solvent in (a) to give a (cyclo)alkylene biscarbamate of the formula $$R^2-O-CO-NH-R^1-NH-CO-O-R^2$$

wherein said reaction is performed in a pressurized distillation reactor at temperatures of 160° to 210° C. at the top of said pressurized distillation reactor and at 180° to 250° C. at the bottom of said pressurized distillation reactor, under a pressure of 7 to 13 bar, wherein said reaction mixture containing crude (cyclo)alkylenebisurea from condensing step (a) is introduced onto a top tray of said pressurized distillation reactor, together with a recycling mixture from process step (e), and an additional amount of said alcohol is introduced into the bottom of said pressurized distillation reactor, with removal of ammonia formed during said reacting step (b), to give said (cyclo) alkylene biscarbamate, (c) removing said ammonia from the vapors obtained at the top of the pressurized distillation reactor of step (b), and from the alcohol obtained by partial condensation of the vapors from step (a), in an alcohol recovery column, wherein ammonia-free alcohol obtained at the bottom of said alcohol recovery column is recycled to provide said additional amount of alcohol which is introduced to the bottom of said distillation reactor of step (a) and to the bottom of said pressurized distillation reactor of step (b), (d) cleaving said (cyclo)alkylene biscarbamate obtained in step (b) in the absence of solvent and in the presence of a catalyst, in a combined cleavage and rectifying column, wherein cleavage occurs in a lower part of said cleavage and rectifying column to provide cleavage products, with a portion of the cleavage products being diverted, and wherein rectification of said cleavage products occurs in an upper part of said cleavage and rectifying column to obtain pure alcohol at the top of said cleavage and rectifying column and crude (cyclo)alkylene diisocyanate is obtained in a lateral takeoff from a mid-portion of said cleavage and rectifying column, (e) reacting said diverted portion of cleavage products from the bottom of said combined cleavage and rectifying column of step (d) with the alcohol from the top of the combined cleavage and rectifying column of step (d) to form a recycling mixture and recycling the recycling mixture into said pressurized distillation reactor of step (b), and (f) distilling said crude (cyclo)alkylene diisocyanate from step (d).

2. The process according to claim 1, wherein said (cyclo)aliphatic diamine, urea and alcohol are present in step (a) in a molar ratio of from 1:2.0 to 2.4:3 to 10.

3. The process according to claim 1, wherein said alcohol is introduced in the bottom of said distillation reactor of step (a) in an amount of from 0.05 to 3 kg/kg of (cyclo)alkylenebisurea formed.

4. The process according to claim 3, wherein said alcohol is introduced in an amount of from 0.1 to 1 kg/kg of (cyclo)alkylenebisurea formed.

5. The process according to claim 1, wherein a residence time in said distillation reactor of step (a) is from 4 to 10 hours preferably 6 to 8 hours.

6. The process according to claim 5, wherein said residence time is from 6 to 8 hours.

7. The process according to claim 1, wherein said alcohol is introduced in the bottom of said pressurized distillation reactor of step (b) in an amount of from 0.5 to 8 kg/kg of (cyclo)alkylene biscarbamate formed.

8. The process according to claim 7, wherein said alcohol is added in an amount of from 1 to 4 kg/kg of (cyclo)alkylene biscarbamate formed.

9. The process according to claim 1, wherein said alcohol added to the bottom of said pressurized distillation reactor of step (b) is removed completely by distillation from the top of said pressurized distillation reactor.

10. The process according to claim 1, wherein energy is supplied to the bottom of said pressurized distillation reactor of step (b) and is regulated to provide a weight ratio of (cyclo)alkylene biscarbamate : alcohol in the bottom of said pressurized distillation reactor of from 0.5 to 1.7.

11. The process according to claim 1, wherein a residence time in said pressurized distillation reactor of step (b) is from 5 to 20 hours.

12. The process according to claim 11, wherein said residence time is from 9 to 14 hours.

13. The process according to claim 1, wherein said alcohol and ammonia formed in step (b) are obtained at the top of said pressurized distillation reactor of step (b), said alcohol is freed from ammonia in said alcohol recovery column at a pressure equal to that of said pressurized distillation reactor, at a column top temperature of at least 60° C. and a bottom temperature of at least 170° C. in said alcohol recovery column.

14. The process according to claim 1, wherein said catalyst is a member selected from the group consisting of halides and oxides of metals of groups IB, IIB, IIIB, IVB, VB, VIB, VIIB and VIIIB of the periodic table.

15. The process of claim 14, wherein said catalyst is a member selected from the group consisting of chlorides of zinc and tin, and oxides of zinc, manganese, iron and cobalt.

16. The process of claim 1, wherein said catalyst concentration, based on the amount of said (cyclo)alkylene biscarbamate employed in step (d), is from 5 to 400 ppm.

17. The process of claim 16, wherein said catalyst concentration is from 20 to 200 ppm.

18. The process according to claim 1, wherein said cleavage and rectifying column of step d is operated with a minimum volume of liquid in the bottom and comprises a falling film evaporator for supplying energy at the bottom of said cleavage and rectifying column, an energy recovery means in a lower third of said cleavage and rectifying column, a means for removing crude (cyclo)alkylene diisocyanate in an upper third of said cleavage and rectifying column and a condenser, condensate collection vessel and pump for reflux and removal of pure alcohol at the top of said cleavage and rectifying column.

19. The process according to claim 18, wherein said means for removing crude (cyclo)alkylene diisocyanate is a lateral take-off.

20. The process according to claim 18, wherein not more than 20% of the amount of the (cyclo)alkylene biscarbamate fed into a falling film evaporator of said pressurized distillation reactor, evaporates, and wherein the (cyclo)alkylene biscarbamate and alcohol vapors generated during reaction are passed in countercurrent fashion 21. The process of claim 1, wherein said diverted portion of the cleavage products of step (d) is equal to from 5 to 50% of the (cyclo)alkylene biscarbamate added.

22. The process of claim 21, wherein said diverted portion of the cleavage products of step (d) is equal to from 15 to 25% of the (cyclo)alkylene biscarbamate added.

23. The process of claim 1, wherein said step (e) is performed in a tubular reactor at a pressure of from 1.7 to 2.3 bar for a residence time of from 1 to 4 hours.

24. The process of claim 23, wherein said pressure is 2 bar.

25. The process of claim 23, wherein said residence time is 2 hours.

* * * * *

UNITED STATES PATENT AND TRADEMARK OFFICE
CERTIFICATE OF CORRECTION

PATENT NO. : 5,360,931
DATED : November 1, 1994
INVENTOR(S) : Gerd BOHMHOLDT et al.

It is certified that error appears in the above-identified patent and that said Letters Patent is hereby corrected as shown below:

COLUMN 8, line 16, "Nectar", should read --Reactor--;
line 46, "reefs", should read --reactor--.

COLUMN 9, lines 3-4, "rescuer", should --reactor--.

COLUMN 12, line 3, "reactoer", should read --reactor--.

COLUMN 13, line 62, "re, crop", should read --reactor--.

COLUMN 15, line 15, please delete "preferably 6 to 8 hours".

Signed and Sealed this

Thirtieth Day of May, 1995

Attest:

BRUCE LEHMAN

Attesting Officer      Commissioner of Patents and Trademarks